United States Patent [19]

Charles et al.

[11] Patent Number: 4,717,665

[45] Date of Patent: Jan. 5, 1988

[54] RECOVERY OF MICROBIAL LIPASE

[75] Inventors: Robert L. Charles, Elkhart; Steven C. Dolby, Middlebury; Chimanbhai P. Patel, Mishawaka; Jayarama K. Shetty, Elkhart, all of Ind.

[73] Assignee: Miles Laboratories, Inc., Elkhart, Ind.

[21] Appl. No.: 863,716

[22] Filed: May 16, 1986

[51] Int. Cl.$^4$ .............................................. C12N 9/20
[52] U.S. Cl. .................................... 435/198; 435/814
[58] Field of Search ............................... 435/198, 814

[56] References Cited

U.S. PATENT DOCUMENTS 4,636,468  1/1987  Arbige et al. ...................... 435/198

OTHER PUBLICATIONS

Methods in Enzymology, vol. 11, (1967), pp. 576-580.

*Primary Examiner*—Lionel M. Shapiro
*Attorney, Agent, or Firm*—Jerome L. Jeffers

[57] ABSTRACT

Disclosed is a method for causing the dissociation of microbial mycelium and extracellular lipase bound thereto and increasing the measurable activity of the lipase. The method involves treating an aqueous suspension of the mycelium with the anhydride of a dicarboxylic acid which results in dissociation of the mycelium and lipase thereby facilitating recovery of the lipase.

10 Claims, 1 Drawing Figure

EFFECT OF SUCCINIC ANHYDRIDE CONCENTRATION ON
LIPASE ACTIVITY IN THE PRESENCE OF FUNGAL MYCELIUM
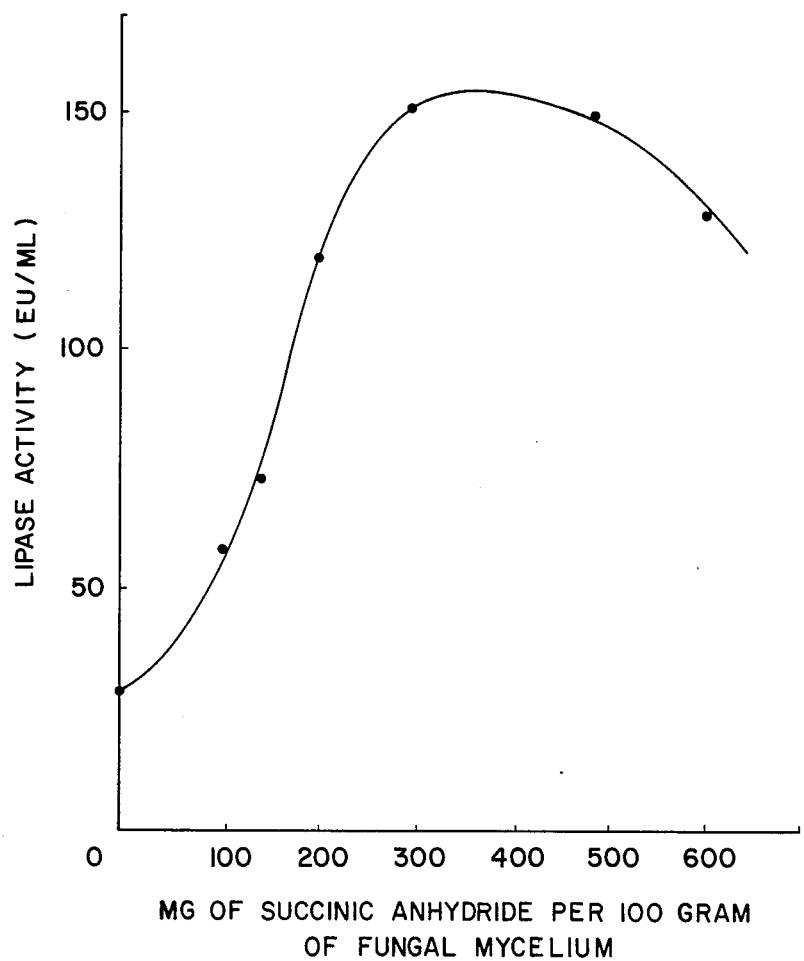

RECOVERY OF MICROBIAL LIPASE

BACKGROUND OF THE INVENTION

The application of lipases for hydrolyzing and/or modifying fats has been recognized for many years. More recently, lipolytic enzymes have been found to be suitable for industrial use. For example, lypolytic enzymes have been found to be useful for improving the milk flavor in certain dairy products. Lipases have also been used by the pharmaceutical industry for inclusion in digestive aids. Other industrial uses for lipolytic enzymes include interesterification of oils and fats, esterification of fatty acids, digestive aids in animal feeds and additives to washing and cleaning products. As a result of the increased acceptance of these applications, the demand for lipases is expected to grow rapidly in the future.

Lipases from animal, plant and microbial origin have been isolated and their properties have been studied extensively. These enzymes catalyze the hydrolysis of water soluble carboxylic acid esters (triglycerides) while the hydrolysis of water soluble carboxylic acid esters by lipase is very slow. The ability to catalyze the hydrolysis of insoluble long chain fatty acid esters thus distinguishes lipases from other esterases which catalyze hydrolysis of soluble esters in preference to insoluble esters.

Microbial lipase is conveniently produced by fermentation with microorganisms such as *Aspergillus niger, Candida cylindracae, Mucor miehei, M. javanicus, Rhizopus delemar, R. arrhizus* and *Pseudomonas fluorescens* which will secrete this enzyme through its cell wall. However, with many microorganisms capable of producing extracellular lipase, a substantial portion of the enzyme apparently remains attached to the cell wall. Sigima and Isobe, 1975, 1976 (Chemical and Pharmaceutical Bulletin, 23, p. 68, 1226 and 24, p. 72) have reported that microbial lipases show exceptionally high surface activity at air water and heptane water interfaces when compared to other groups of proteins. This high surface activity results in a strong adsorption of the lipase onto hydrophobic surfaces of the cell wall. This phenomenon has been observed in conjunction with microbial lipase secreted by a fungus of the species *Mucor miehei*.

In the case of fermentation of the fungal species *Mucor miehei*, more than 99% of the extracellular lipase produced is bound to the fungal mycelium while extracellular microbial rennet also produced by this organism is distributed freely in the fermentation broth. In U.S. Pat. No. 3,899,395 there is disclosed a method for recoverying microbial lipase from the fermentation growth product of a Mucor species which involves adsorbing the fermentation growth product with a material selected from diatomaceous earth or clay at a pH of from 4 to 6 and then eluting the lipolytic enzyme by adjusting the pH to a range of from 9 to 11.

SUMMARY OF THE INVENTION

The present invention is an improvement in the method of producing microbial lipase by the growth of a suitable microbial strain in a nutrient growth medium which results in the formation of microbial mycelium having lipase bound thereto. The improvement involves contacting an aqueous dispersion of the mycelium with an anhydride of an organic acid to thereby achieve separation of the mycelium and lipase.

DESCRIPTION OF THE INVENTION

In practicing this invention, the lipase secreting microorganism is grown in a suitable nutrient growth medium and the mycelium containing mycelial bound lipase is separated from the fermentation beer. Typically, the mycelium is separated from the culture filtrate by centrifugation and washed with deionized, distilled water. The mycelium is then resuspended in water and the pH adjusted to a level within the range of from 7 to 9, preferably 7.5 to 8.5, and ideally to 8.0 using 3N NaOH or KOH. The amount of acid anhydride employed will typically range from 0.2 to 0.6 g anhydride per 100 gm of mycelium on a dry weight basis. After stabilization of the pH, the suspension is further stirred for another hour and centrifuged. The clear supernatant is used for checking the lipase activity.

Lipase activity is determined by measuring butyric acid liberated from tributyrin substrate using a pH-stat under standard conditions, i.e. pH 6.2 at 42° C. One lipase unit (EW) is defined as the activity of enzyme which liberates one micromole of butyric acid per minute under the experimental conditions.

$$\text{One lipase unit} = \frac{\text{Volume of alkali consumed} \times \text{molarity of alkali}}{\text{Incubation time (minutes)} \times \text{volume of enzyme dilution factor} \times 10^3}$$

The object of the present invention, derivatization of the cell bound enzyme, is accomplished by contacting the enzyme with an organic carboxylic acid anhydride. Any anhydride which will accomplish this goal may be used. Particularly suitable anhydrides are derived from acetic acid and organic dicarboxylic acids such as succinic, maleic and citraconic; succinic anhydride is preferred.

While the invention is not predicated on any particular theory or mechanism, it is believed that treatment of the mycelial bound lipase with an acid anhydride results in the substitution of cationic $NH_3+$ groups with anionic $COO-$ groups thereby producing a net change of two charge units per each modified amino group. This increase in the electronegativity of the enzyme/protein destabilizes the stable mycelial/lipase complex resulting in the separation of the lipase and mycelium as indicated:

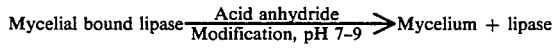

Mycelial bound lipase $\xrightarrow[\text{Modification, pH 7-9}]{\text{Acid anhydride}}$ Mycelium + lipase Upon achieving this separation, the mycelium is separated from the aqueous phase by conventional solid/liquid separatory techniques whereupon the aqueous phase containing the lipase is processed further to provide the desired product. More particularly the mycelium is separated by centrifugation and the clear supernatant is further concentrated by vacuum evaporation.

In the following examples, fungal mycelium containing mycelial bound lipase was separated from the fermentation beer obtained from *Mucor miehei*. The microorganism was grown under aerobic conditions in a fermentation medium consisting of soy meal, starch and corn steep liquor at pH 6.1–6.5 and 32° C. for 3–4 days.

EXAMPLE I

Fungal mycelium (free from culture filtrate) obtained from 1000 ml of fermentation broth produced during the culturing of *Mucor miehei* was washed once with deionized distilled water. The washed mycelial cake was resuspended in water (1000 ml) and the pH was adjusted to 8.0 using 3N NaOH. Various amounts of succinic anhydride were added in small increments to 100 ml aliquots of the aqueous suspension of mycelium with constant stirring at 25° C. The pH was maintained between 7.5 and 8.0 with 3N NaOH during addition of the anhydride. After complete addition of the anhydride, the suspension was stirred for another hour and insolubles were separated by centrifugation at 15,000 rpm for 30 minutes at 5° C. The effect of succinic anhydride concentration on the release of lipase was determined by measuring the lipase activity. The drawing represents lipase activity as a function of succinic anhydride concentration.

Referring to the drawing, it can be determined that an aqueous extraction of fungal mycelium contained only 28 lipase units/ml. Addition of succinic anhydride during extraction of lipase at pH 8.0 caused a marked increase in the lipase activity. The lipase activity of the supernatant was increased with increasing concentration of succinic anhydride and reached a maximum of about 128 lipase units/ml (4.8× over the control). The marked increase in the lipase activity after succinylation of fungal mycelium could have been due to activation of lipase by succinylation as well as desorption of the enzyme from the fungal mycelium.

EXAMPLE II

Five hundred grams of washed mycelium were suspended in 500 ml of deionized distilled water and the pH was adjusted to 8.0 using 3N NaOH. The suspension was stirred for one hour and solubilized lipase was separated from the mycelium by centrifugation (15,000 rpm for 30 minutes at 5° C.). To the clear supernatant (50 ml containing 28 lipase units/ml) various amounts of succinic anhydride were added as described in Example I. After stabilization of the pH, the lipase activity was measured and is represented in Table 1.

TABLE 1

Effect of Succinylation of Lipase on the Lipase Activity

| Succinic Anhydride Added to 100 ml Aliquot | Lipase Activity EU/ml |
| --- | --- |
| 0 | 28 |
| 100 mg | 35 |
| 150 mg | 52 |
| 200 mg | 68 |
| 400 mg | 60 |
| 600 mg | 50 |

Succinylation of lipase alone increased the lipolytic activity by greater than 100%. Thus the observed marked increase in the lipase activity after derivatization of the fungal mycelium was not only due to the activation of the enzyme but also to the release of mycelial bound enzyme.

EXAMPLE III

One hundred milliliters of fungal mycelial suspension was adjusted to pH 8.0 using 3N NaOH. Various amounts of acetic anhydride were added and acetylation was carried out at pH 8.0 as described above. After stabilization of the pH, the suspension was centrifuged and the lipase activity of the supernatant was determined as indicated by Table 2.

TABLE 2

Effect of Acetylation of Fungal Mycelium on the Release of Lipase

| Amount of acetic anhydride per 100 ml fungal mycelium | Lipase activity EU/ml |
| --- | --- |
| 0 | 28 |
| 0.1 ml | 20 |
| 0.3 ml | 28 |
| 0.5 ml | 38 |
| 0.7 ml | 50 |
| 1.0 ml | 30 |

Acetylation of the fungal mycelium also caused the release of mycelial bound lipase. However, acetylation was found to be less effective than succinylation. The difference could be due to the marked increase in the electronegativity of the enzyme molecule by succinylation.

EXAMPLE IV

In another experiment, the pH of washed fungal mycelium (100 ml) was adjusted to 8.0 using 3N NaOH. Solid succinic anhydride (300 mg) was added in small increments with constant stirring while the pH was maintained between 7.5 and 8.5 using 3N NaOH. After the addition of succinic anhydride, the suspension was stirred for another hour at 25° C. and the lipase was separated by centrifugation at 15,000 rpm for 30 minutes at 5° C. The activity of the enzyme was measured at various pH's at 30° C. as described earlier. For comparison, the activity of lipase (control) extracted in the absence of succinic anhydride was also measured at different pH's as indicated in Table 3.

TABLE 3

Effect of pH on the Activity of Lipase and Succinylation Lipase

| | % of Maximum Activity | |
| --- | --- | --- |
| Assay pH | Lipase | Succinylated Lipase |
| 5.0 | 52 | 81 |
| 6.0 | 80 | 100 |
| 6.5 | 90 | 98 |
| 7.0 | 100 | 94 |
| 7.5 | 95 | 84 |
| 8.0 | 80 | 70 |
| 9.0 | 60 | 39 |

Lipase exhibited maximum activity at pH 7.0 and 30° C. However, succinylation of the lipase caused a shift in the pH for the maximum activity towards the acid side, i.e. pH 6.0. It is possible that the net increase in the electronegativity of the lipase molecule by succinylation may have increased the stability of the enzyme against acidic pH conditions.

What is claimed is:

1. In combination with the preparation of microbial lipase by the growth of a species of microorganism in a suitable nutrient growth medium which results in the formation of microbial mycelium having lipase bound to the surface thereof the improvement which comprises contacting a water dispersion of the mycelium having lipase bound thereto with an anhydride of an organic acid at a pH of 7 to 9 to thereby separate the lipase from the mycelium.

2. The method of claim 1 wherein the pH is from 7.5 to 8.5.

3. The method of claim 1 wherein the pH is 8.

4. The method of claim 1 wherein the microorganism is selected from the species of *Aspergillus niger, Candida cylindracae, Mucor miehei, M. javanicus; Rhizopus delemar, R. arrhizus* and *Pseudomonas fluorescens.*

5. The method of claim 1 wherein the species is *Mucor miehei.*

6. The method of claim 1 wherein the anhydride is derived from acetic, succinic, maleic or citraconic acid.

7. The method of claim 1 wherein the anhydride is succinic anhydride.

8. The method for increasing the measurable activity of microbial lipase which is produced during the growth of a suitable species of microorganism in a suitable growth medium which growth results in the formation of microbial mycelium having lipase bound thereto comprising contacting an aqueous dispersion of the microbial mycelium with an anhydride of a suitable organic acid at a pH of from 7.5 to 8.5.

9. The method of claim 8 wherein the anhydride is succinic anhydride.

10. The method of claim 8 wherein the microorganism is a fungus of the species *Mucor miehei.*

* * * * *